(12) United States Patent
Koroulis et al.

(10) Patent No.: US 6,558,907 B2
(45) Date of Patent: May 6, 2003

(54) METHODS AND COMPOSITIONS FOR ARRAYING NUCLEIC ACIDS ONTO A SOLID SUPPORT

(75) Inventors: Melanie C. Koroulis, Corning, NY (US); Santona Pal, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/859,160

(22) Filed: May 16, 2001

(65) Prior Publication Data

US 2002/0187476 A1 Dec. 12, 2002

(51) Int. Cl.$^7$ .................. C12Q 1/68; C12P 19/34; C12M 1/34; C07H 21/02; C07H 21/04
(52) U.S. Cl. ............... 435/6; 435/7.1; 435/91.1; 435/91.2; 435/287.2; 536/22.1; 536/23.1; 536/24.3; 536/24.31; 536/24.32; 536/24.33
(58) Field of Search ............... 435/6, 7.1, 91.1, 435/91.2, 287.2; 536/22.1, 23.1, 24.3–24.33

(56) References Cited

U.S. PATENT DOCUMENTS

| | | | |
|---|---|---|---|
| 5,141,813 A | | 8/1992 | Nelson .................. 428/402 |
| 5,521,061 A | * | 5/1996 | Bresser et al. .................. 435/5 |
| 5,631,322 A | | 5/1997 | Veronese et al. ........... 525/54.1 |
| 5,700,637 A | | 12/1997 | Southern ..................... 435/6 |
| 5,800,992 A | | 9/1998 | Fodor et al. .................. 435/6 |
| 5,807,522 A | | 9/1998 | Brown et al. ................. 422/50 |
| 5,972,692 A | * | 10/1999 | Hashimoto et al. ....... 435/285.2 |

FOREIGN PATENT DOCUMENTS

| | | |
|---|---|---|
| WO | WO 94/00600 | 1/1994 |
| WO | WO 95/35505 | 12/1995 |
| WO | WO 99/05308 | 2/1999 |
| WO | WO 00/01798 | 1/2000 |

OTHER PUBLICATIONS

Maniatis et al Molecular Cloning A Laboratory Manual p. s1.1011.104 1989.*

R. Maldonado–Rodriguez et al., "Hybridization of Glass–Tethered Oligonucleotide Probes to Target Strands Preannealed With Labeled Auxiliary Oligonucleotides", Molecular Biotechnology, vol. 11, 1999.

* cited by examiner

*Primary Examiner*—Jeffrey Siew
(74) *Attorney, Agent, or Firm*—Thomas R. Beall; Vincent T. Kung

(57) ABSTRACT

The present invention provides a method for depositing a nucleic acid on a solid support. The method comprises contacting a solid support with a solution of nucleic acid, the solution comprising about 30% to about 80% dimethylsulfoxide (DMSO) by volume, sodium chloride and sodium citrate salt containing buffer (SSC) at a final concentration of from about 0.1× (15 mM sodium chloride+1.5 mM sodium citrate) to about 0.8× (120 mM sodium chloride+12 mM sodium citrate). The composition includes a nucleic acid at a concentration ranging from 0.01 mg/ml to 0.50 mg/ml. Preferably, the solution comprises about 40% to about 80% DMSO by volume and SSC at a final concentration from about 0.1× to about 0.5×. More preferably, the solution comprises about 40% to about 60% DMSO by volume and SSC at final concentration from about 0.25× to about 0.5×. Most preferably, the solution comprises about 50% DMSO by volume and SSC at a final concentration of about 0.25×. The nucleic acid is preferably a double stranded DNA or an oligonucleotide.

25 Claims, 9 Drawing Sheets

(9 of 9 Drawing Sheet(s) Filed in Color)

*After bioformating, t = 0*

*After 15 days, t = 15 days*

4 days after bioformating -

21 days after bioformating -

METHODS AND COMPOSITIONS FOR ARRAYING NUCLEIC ACIDS ONTO A SOLID SUPPORT

BACKGROUND OF THE INVENTION

1. Field of the Invention

The present invention relates to methods and compositions for fabrication of high-density nucleic acid arrays for use in biological assays.

2. Background

Hybridization is a hydrogen-bonding interaction between two nucleic acid strands that obey the Watson-Crick complementary rules. All other base pairs are mismatches that destabilize hybrids. Since a single mismatch decreases the melting temperature of a hybrid by up to 10° C., conditions can be found in which only perfect hybrids can survive. Many hybridization experiments can be simultaneously carried out on a single solid support on which multiple nucleic acids "probes" have been immobilized by either covalent or non-covalent methods. The tethered "probe" is hybridized with target nucleic acids that usually bear a radioactive, fluorescent label, or haptens that could be visualized by chemiluminescent or other detection methods. The resulting hybrids are separated from the unreacted labeled strands by washing the support. Hybrids are recognized by detecting the label bound to the surface of the support.

Oligonucleotide hybridization is widely used to determine the presence in a nucleic acid of a sequence that is complimentary to the oligonucleotide probe. In many cases, this provides a simple, fast, and inexpensive alternative to conventional sequencing methods. Hybridization does not require nucleic acid cloning and purification, carrying out base-specific reactions, or tedious electrophoretic separations. Hybridization of oligonucleotide probes has been successfully used for various purposes, such as analysis of genetic polymorphisms, diagnosis of genetic diseases, cancer diagnostics, detection of viral and microbial pathogens, screening of clones, genome mapping and ordering of fragment libraries.

An oligonucleotide array is comprised of a number of individual oligonucleotide species tethered to the surface of a solid support in a regular pattern, each species in a different area, so that the location of each oligonucleotide is known. An array can contain a chosen collection of oligonucleotides, e.g., probes specific for all known clinically important pathogens or specific for all known clinically important pathogens or specific for all known sequence markers of genetic diseases. Such an array can satisfy the needs of a diagnostic laboratory. Alternatively, an array can contain all possible oligonucleotides of a given length n. Hybridization of a nucleic acid with such a comprehensive array results in a list of all its constituent n-mers, which can be used for unambiguous gene identification (e.g., in forensic studies), for determination of unknown gene variants and mutations (including the sequencing of related genomes once the sequence of one of them is known), for overlapping clones, and for checking sequences determined by conventional methods. Finally, surveying the n-mers by hybridization to a comprehensive array can provide sufficient information to determine the sequence of a totally unknown nucleic acid.

Oligonucleotide arrays can be prepared by synthesizing all the oligonucleotides, in parallel, directly on the support, employing the methods of solid-phase chemical synthesis in combination with site-directing masks as described in U.S. Pat. No. 5,510,270. Four masks with non-overlapping windows and four coupling reactions are required to increase the length of tethered oligonucleotides by one. In each subsequent round of synthesis, a different set of four masks is used, and this determines the unique sequence of the oligonucleotides synthesized in each particular area. Using an efficient photolithographic technique, miniature arrays containing as many as $10^5$ individual oligonucleotides per $cm^2$ of area have been demonstrated.

Another technique for creating oligonucleotide arrays involves precise drop deposition using a piezoelectric pump as described in U.S. Pat. No. 5,474,796. The piezoelectric pump delivers minute volumes of liquid to a substrate surface. The pump design is very similar to the pumps used in ink jet printing. This picopump is capable of delivering 50 micron diameter (65 picoliter) droplets at up to 3000 Hz and can accurately hit a 250 micron target. The pump unit is assembled with five nozzles array heads, one for each of the four nucleotides and a fifth for delivering, activating agent for coupling. The pump unit remains stationary while droplets are fired downward at a moving array plate. When energized, a microdroplet is ejected from the pump and deposited on the array plate at a functionalized binding site. Different oligonucleotides are synthesized at each individual binding site based on the microdrop deposition sequence.

A popular method for creating high-density arrays utilizes pins that are dipped into solutions of the sample fluids and then touched to a surface. The nucleic acid, e.g., DNA, is typically solubilized in an aqueous medium (also sometimes referred to as an "ink") that contains salts, which are used as components of buffers that are compatible with biological macromolecules. 3×SSC (450 mM sodium chloride and 45 mM sodium citrate) is a standard printing ink. See, e.g., U.S. Pat. No. 5,807,522 (Example 1).

Printing with 3×SSC is considered useful since the salt particles that are deposited on the arrays after printing enable the verification of the printing process. This verification can be achieved by an imaging method that uses the principle of compound microscopy to photograph printed grids of an HDA, and then electronically determine the presence or absence of the salt spots printed with DNA. By using an oblique white light source, principally the salt deposits are detected by the imaging method (also referred to herein as the 100% Dot Inspection System) and not DNA. Therefore, if one wishes to use such a verification process it is imperative that the ink contains salts.

However, the use of SSC inks can be problematic. The first problem encountered in manufacturing DNA arrays using a 3×SSC ink is that the rate of evaporation of the aqueous medium is very high compared to the time required to print multiple slides. This is a major obstacle to scaling up the manufacturing process. Additionally, it has been observed by the present inventors that not only is the 3×SSC ink incapable of printing the required number of slides but variable arrays result due to a rapidly changing concentration of DNA because of the evaporation of aqueous medium.

Therefore, there is a need for an ink composition for printing HDA of nucleic acids that overcome the disadvantages seen in the art.

SUMMARY OF THE INVENTION

In an attempt to solve the problem related to evaporation discussed above, we tested an ink composition consisting of 50% DMSO (dimethylsulfoxide) by volume and SSC at a final concentration of 1× (150 mM NaCl+15 mM sodium citrate). This composition was considered optimal since DMSO is an organic solvent with high vapor pressure and it is highly miscible with water. Moreover, DMSO is a hygroscopic solvent and is thereby able to compete with the net losses of the solvent due to evaporation of the aqueous component by absorbing moisture from the air. The 1:1 ratio of DMSO and SSC was found to give minimal evaporation of the ink over several print runs and was successfully used to print various HDAs.

To further test the ink, genetic material was suspended in the 1:1 DMSO:SSC (1×) composition and used to print human and yeast arrays using the contact printing method. Many arrays were printed on CMT-GAPS™ glass slides (Corning) with this ink for over a period of 2 months and the hybridization performance obtained on these slides was acceptable. However, after ~4–5 weeks, these genetic materials failed to give satisfactory hybridization performance. After repeated failed attempts at printing this DNA, the genetic materials were analyzed for the presence of contaminants that could potentially degrade the DNA (for example the DNase enzyme is a common cause of DNA degradation). Gel electrophoreses of the DNA samples showed that a large number of the fragments did not exhibit their expected mobility. Instead the DNA appeared to be retained in the wells of the gel. Such an anomalous behavior is generally associated with the formation of large aggregates of DNA that are not able to travel through the sieving material of the gel matrix. Based on the gel analysis it was clear that the integrity of the DNA molecules had been compromised. Visual inspection of the ink indicated the presence of particulate matter. Infra-red analysis of these particles indicated the presence of sodium citrate and DNA. Further solubility studies on the ink (in the absence of the DNA) indicated that the ink was inherently unstable and was prone to causing the precipitation of the citrate component. The analytical data suggested that the components of the ink resulted in aggregation of the DNA over a period of time.

We have now surprisingly discovered that lowering the final SSC concentration in the ink to about 0.8× (120 mM sodium chloride+12 mM sodium citrate) to about 0.1× (15 mM sodium chloride+1.5 mM sodium citrate), and having the DMSO concentration between about 30% to about 80% by volume, results in an ink composition that provides superior adhesion, hybridization efficiency and hybridization response from nucleic acid species that are printed on positively charged substrates for nucleic acid binding (e.g., an aminated surface).

We also discovered that unexpectedly the ink of the present invention having a salt concentration significantly lower than the 3×SSC industry standard enables superior imaging of a highly dense array of printed spots of DNA using a visible light source device. We have further discovered that the ink composition of the present invention satisfies another need in the art in that it enables the long-term storage of the nucleic acid, and thus facilitates the manufacture of HDAs at a high throughput over a long period of time, e.g., over 7 weeks.

We have further unexpectedly discovered that the ink of the present invention having a DMSO concentration greater than 60% by volume results in increased denaturation of the nucleic acid. Even more unexpected is the discovery that this denaturation increases over time. Thus, a lower concentration of DMSO can be used if the time the DNA is suspended in the ink before printing is increased. For example, double stranded DNA in inks containing DMSO at 50% or greater v/v for 21 days showed signs of denaturation. See, FIGS. 6A, 6B, 7A and 7B.

In one embodiment the present invention provides a method for depositing a nucleic acid on a solid support. The method comprises contacting a solid support with a solution of nucleic acid, the solution comprising about 30% to about 80% dimethylsulfoxide (DMSO) by volume, and sodium chloride and sodium citrate salt containing buffer (SSC) at a final concentration of from about 0.1× (15 mM sodium chloride+1.5 mM sodium citrate) to about 0.8× (120 mM sodium chloride+12 mM sodium citrate). The composition includes a nucleic acid at a concentration ranging from 0.01 mg/ml to 0.50 mg/ml. Preferably, the solution comprises about 40% to about 80% DMSO by volume and SSC at a final concentration from about 0.1× to about 0.5×. More preferably, the solution comprises about 40% to about 60% DMSO by volume and SSC at final concentration from about 0.25× to about 0.5×. Most preferably, the solution comprises about 50% DMSO by volume and SSC at a final concentration of about 0.25×. The nucleic acid is preferably a double stranded DNA or an oligonucleotide.

In the method any solid support can be used as long as it is capable of retaining the printed nucleic acid. Preferably, the solid support is a two dimensional solid glass surface (for example, a commercially available 3"×1" microscope glass slides made of soda lime or other glass compositions) or a three dimensional porous glass surface (for example, Vycor™, (Corning Inc.)) or a porous glass substrates made from porous pyrex glass by tape-cast or sol-gel processes. It is preferred that the glass have a surface that is coated to facilitate the adhesion of the nucleic acid. An aminated surface coating is preferred. The aminated surface can comprise, for example, gamma-aminopropyl silane or polyl-ysine.

The contacting step of the method includes, for example, immersing the tip of a pin into the nucleic acid ink solution. The pin can be solid or hollow. The tip of the pin is then removed from the solution to provide solution adhered to the tip. The solution adhering to the tip is then contacted with a solid support to thereby transfer the solution from the tip to the solid support. To form a nucleic acid patterned in an array the contacting step is repeated a plurality of times. This can be accomplished, for example, by use of a typographic pin array.

To facilitate denaturation of the nucleic acid, the nucleic acid may be suspended in the DMSO/SSC composition for at least 1 day prior to printing, preferably at least 5 days, more preferably at least 10 days, still more preferably at least 15 days.

In another embodiment, the present invention provides a nucleic acid printing ink composition comprising about 30% to about 80% dimethylsulfoxide (DMSO) by volume, SSC at a final concentration of from about 0.1× to about 0.8× and water. The composition can further include a nucleic acid at a concentration ranging from 0.01 mg/ml to 0.5 mg/ml. The nucleic acid is preferably a double stranded DNA or an oligonucleotide. The composition may also include EDTA in a final concentration between 0 and 4 mM, preferably 0.5 mM.

Other agents can be incorporated as part of the ink composition including those that would change the viscosity of the ink for enhancing wettability for certain printing conditions, for example, glycerol, poly-ethylene glycol, histone proteins etc. The inks may also contain small amounts of polycationic agents such as poly-lysine, spermine etc.

Preferably, the solution comprises about 40% to about 80% DMSO by volume and SSC at a final concentration from about 0.1× to about 0.5×. More preferably, the solution comprises about 40% to about 60% DMSO by volume and SSC at final concentration from about 0.25× to about 0.5×.

Most preferably, the solution comprises about 50% DMSO by volume and SSC at a final concentration of about 0.25×. The nucleic acid is preferably a single or double stranded DNA or an oligonucleotide.

Other aspects of the invention are disclosed infra.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Row 1 (across): 1.5 kB DNA fragment in 50%DMSO:SSC (1×, 150.0 mM NaCl, 15.0 mM Na citrate)

Row 2: 1.5 kB DNA fragment in 50%DMSO:SSC (0.5×, 75.0 mM NaCl, 7.5 mM Na citrate)

Row 3: 1.5 kB DNA fragment in 50%DMSO:SSC (0.25×, 37.5 mM NaCl, 3.75 mM Na citrate)

Row 4: 1.5 kB DNA fragment in 50%DMSO:water

Figure 4A:
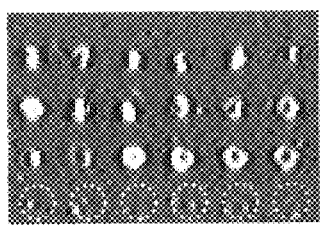
FIGS. 4A, 4B and 4C are three separate images. In each image 50% DMSO:SSC based inks with varying concentrations of the SSC were used to bio-format a 1.5 Kb fragment of DNA. These DNA inks were printed on the CMT-GAPS (TM) slides with a robotic printer using stainless steel pins. The grid layout for the different inks is set forth below.

FIG. 4A shows the raw image of the printed dots from the 100% Dot Inspection System. The dotted circles on the grid indicates the set of printed dots that could not be imaged due to the absence of any salts in the ink.

Figure 4B:
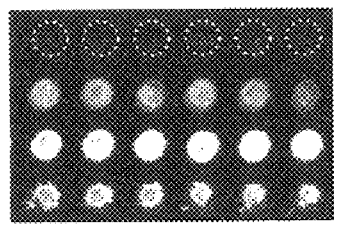

FIG. 4B represents a portion of the grid on the printed slide that has been stained with sybr gold dye. Sybr gold is a fluorescent dye and is used as a qualitative indicator of the presence of DNA. The image indicates that significant amounts of DNA is deposited and retained with 50% DMSO based inks with SSC concentrations of less than 0.5× to inks containing no salt. The dotted circles on the grid indicates the set of printed DNA with 50%DMSO:SSC at 1×SSC concentration that did not stain significantly with sybr gold. The morphology of spots with no SSC in the ink is different from those containing SSC.

Figure 4C:
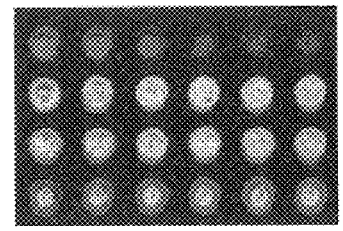

FIG. 4C represents a pseudo-color image of the signals obtained from hybridization of the DNA printed with the DMSO:SSC based inks. The hybridizations were carried out with a Cy3 labeled 1.5 kB DNA. The slide was scanned on Scan Array 3000 (General Scanning Inc.). The data from the image indicates that comparable hybridization signal is obtained with 50% DMSO:SSC inks containing SSC at concentrations between 0.5× and 0.1×SSC. DMSO:SSC compositions containing salt concentrations that is in between 1× and 0.5× have hybridization signals that is lower than that obtained with 0.5× and higher than that obtained with 1.0×. Ink compositions having no salt have poor dot morphology.

Figure 5:
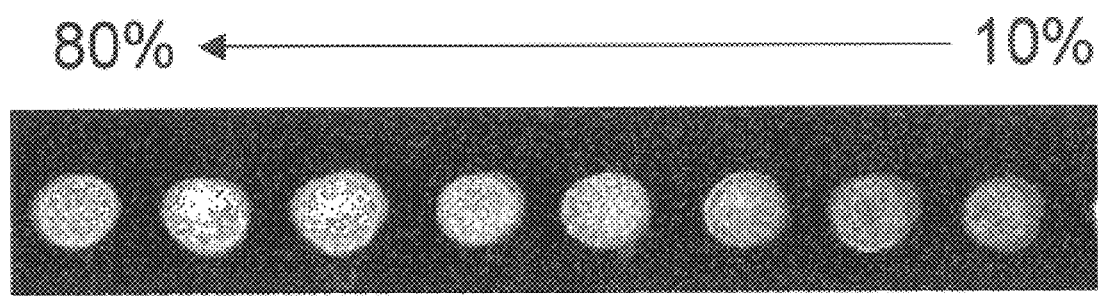

FIG. 5 is an image representing a pseudo-color image of a hybridization done on a array of DNA dots spotted with a variety of DMSO:SSC based inks in which the salt concentration has been kept constant at 0.25×SSC and the amount of DMSO has been varied from 10 to 80% v/v. The relative fluorescence units of signal from hybridization increases with increasing concentration of DMSO up to 70–80% DMSO.

Figure 6A:
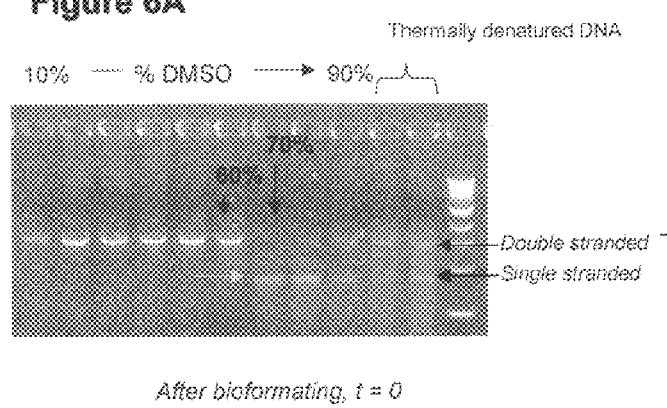
Figure 6B:
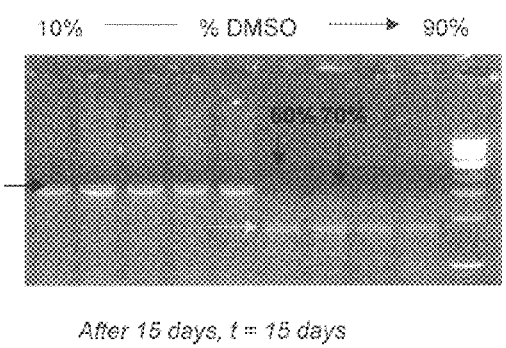

FIGS. 6A and 6B depict images of agarose gels indicating the conformational state of DNA that is exposed to DMSO based inks that do not contain any salts. The enhancement in hybridization signal from DNA in DMSO inks is expected to be in part due to the effect of denaturation of the DNA. Panel A shows an agarose gel of DNA suspended in increasing concentration of DMSO. The electrophoretic mobility of the DNA suspended in >60% DMSO inks suggests the presence of denatured DNA containing both double and single stranded DNA species. Thermally denatured DNA suspended in water were run alongside as controls to establish the expected mobility of the denatured 1.5 kB DNA. Panel B shows that the denaturing potential of DMSO increases with time. With increasing time, inks containing DMSO at greater than 50% v/v begin to show signs of denaturation.

Figure 7A:
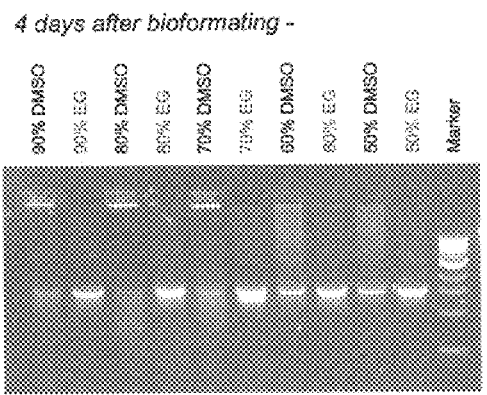
Figure 7B:
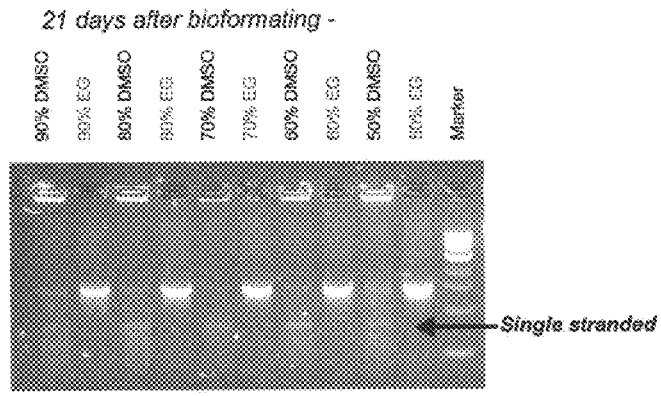

FIGS. 7A and 7B depict agarose gels showing the conformational state of a 1.5 kB DNA exposed to inks differing in the concentration of DMSO or Ethylene glycol (EG) for 4 days. The salt concentration in these inks have been kept constant at 0.25×SSC to monitor the effect of the organic component only. The change in the conformational state of the same DNA samples as a function of time is shown in FIG. 7B. The appearance of new bands in the DMSO based inks (in contrast to the EG based inks) with electrophoretic mobility similar to that of single stranded fragments suggests denaturation of the DNA by DMSO.

DETAILED DESCRIPTION OF THE INVENTION

The invention provides for methods and compositions for depositing nucleic acids on a solid support. The composition of the invention, also called a "printing ink" or "ink", contains about 30% to about 80% dimethylsulfoxide (DMSO) by volume, sodium chloride and sodium citrate salt containing buffer (SSC) at a final concentration of from about 0.1× (15 mM sodium chloride+1.5 mM sodium citrate) to about 0.8× (120 mM sodium chloride+12 mM sodium citrate). The composition may also include a nucleic acid at a concentration ranging from 0.01 mg/ml to 0.50 mg/ml. It has been surprisingly discovered that the ink composition of the present invention provides superior adhesion, hybridization efficiency and hybridization response from nucleic acid species that are printed on positively charged substrates for nucleic acid binding (e.g., an aminated surface) than the 3×SSC standard industry ink.

It has also be surprisingly discovered that the ink of the present invention enables superior imaging of a highly dense array of printed spots of DNA using a visible light source device. It has further been discovered that the ink composition of the present invention enables the long-term storage of the nucleic acid, and thus facilitates the manufacture of arrays at a high throughput over a long period of time.

The nucleic acid used in the method and composition of the invention may be ribonucleic acid (RNA) or deoxyribonucleic acid (DNA). The nucleic acid may be single or double stranded. Oligonucleotides (synthetic nucleic acids) may also be used. The nucleic acid may be a PCR product, PCR primer, or nucleic acid duplex, to list a few examples. The typical concentration of nucleic acid in the ink solution is preferably 0.01 mg/ml to 0.50 mg/ml and more preferably 0.25 mg/ml.

The invention provides a method for depositing a nucleic acid onto a solid support. The method includes the step of contacting a solid support with a solution of nucleic acid, the solution comprising about 30% to about 80% dimethylsulfoxide (DMSO) by volume, sodium chloride and sodium citrate salt containing buffer (SSC) at a final concentration of from about 0.1× (15 mM sodium chloride+1.5 mM sodium citrate) to about 0.8× (120 mM sodium chloride+12 mM sodium citrate) and a nucleic acid at a concentration ranging from 0.01 mg/ml to 0.50 mg/ml.

In a preferred embodiment, the contacting step includes the steps of immersing a tip of a pin into the solution of nucleic acid; removing said tip from the solution to provide solution adhered to said tip; and contacting the solution with a solid support to thereby transfer the solution from the tip to the solid support. In a more preferred embodiment, the contacting step is accomplished robotically. Such robotic systems are well know and are available commercially from, for example, Intelligent Automation Systems (IAS), Cambridge, Mass.

The pin can be solid or hollow. The tips of solid pins are generally flat, and the diameter of the pins determines the volume of fluid that is transferred to the substrate. Solid pins having concave bottoms can also be used. To permit the printing of multiple arrays with a single sample loading, hollow pins that hold larger sample volumes than solid pins and therefore allow more than one array to be printed from a single loading can be used. Hollow pins include printing capillaries, tweezers and split pins. A preferred split pen is the micro spotting pin developed by TeleChem International (Sunnyvale, Calif.).

A typographical pin array having a matrix of pins aligned such that each pin from the matrix fits into a corresponding source well, e.g., a well from a microtiter plate, is preferably used to form a high density array.

The solid support preferably has a planar surface upon which the nucleic acid is deposited. The solid support is generally a glass slide, substrate or membrane. A two dimensional solid glass surface or a three dimensional porous glass surface may be used.

The glass surface may be coated to facilitate adhesion of the printed nucleic acid. An aminated surface coating is preferred. Amination techniques are well know in the art. Gamma-aminopropyl silane and polylysine are preferred aminating agents. Gamma-aminopropyl silane coated slides (CMT-GAPS™ glass slides) are available commercially from Corning Inc.

The arrays produced in accordance with the methods of the present invention may be interrogated by targets (e.g., oligonucleotides, nucleic acid fragments such as cDNA and cRNA, PCR products, etc.) which are labeled. For example, the targets may be labeled with fluorophores such as the Cy3, Cy5, Alexa dyes etc. or labeled with other haptens such as biotin, digoxogenin. The methods for biotinylating nucleic acids are well known in the art and are adequately described by Pierce (Avidin-Biotin Chemistry: A Handbook. Pierce Chemical Company, 1992, Rockford Ill.).

To detect the hybridization event (i.e., the presence of the biotin), the solid support is incubated with streptavidin/horseradish peroxidase conjugate. Such enzyme conjugates are commercially available from, for example, Vector Laboratories (Burlingham, Calif.). The streptavidin binds with high affinity to the biotin molecule bringing the horseradish peroxidase into proximity to the hybridized probe. Unbound streptavidin/horseradish peroxidase conjugate is washed away in a simple washing step. The presence of horseradish peroxidase enzyme is then detected using a precipitating substrate in the presence of peroxide and the appropriate buffers.

It is also possible to use chemiluminescent substrates for alkaline phosphatase or horseradish peroxidase (HRP), or fluorescence substrates for HRP or alkaline phosphatase. Examples include the diox substrates for alkaline phosphatase available from Perkin Elmer or Attophos HRP substrate from JBL Scientific (San Luis Obispo, Calif.).

Method for fabrication and use of high density nucleic acid arrays are set forth in *Microarray Biochip Technology*, M. Schena, ed. Eaton Publishing, Natick, Mass. (2000).

The documents cited throughout the specification are incorporated herein by reference.

EXAMPLES

Example 1

As noted above in the Summary of the Invention, it was hypothesized that the prior ink composition was unstable and the sodium citrate contributed significantly to the initiation of the precipitation or aggregation of the DNA. Five different inks that differed in the composition of the aqueous buffers were evaluated for their printing performance. Each of the compositions that were tested either reduced or removed the sodium citrate component in the ink. The criteria for an acceptable ink were (1) to obtain a good hybridization response from printed DNA, (2) to retain the ability to carry out dot detection for quality control purposes, (3) and to maintain DNA integrity over a long period of time.

To limit the problems due to evaporation, all inks were designed to contain 50% DMSO by volume. The 100% Dot Inspection System relies on the ability to image salt deposits following printing. Previous experiments had indicated that the ability to accurately image arrays was dependent on the amount of salts in the ink. A salt concentration in the range of 13 g/l (as in the 50% DMSO:SSC (1×)) was found to be sufficient to enable detection of the printed dots. Hence this experiment was designed such that all compositions (except composition #4) contained a total salt concentration of 13.178 g/l. A detailed description of the ink compositions is described below. The six different compositions were as follows 1) 50% DMSO: NaCl+Na citrate (1×)—printed as a control
2) 50% DMSO: KCl+Na citrate
3) 50% DMSO: NaCl+K citrate
4) 50% DMSO: NaCl+Na citrate (0.5×)
5) 50% DMSO: NaCl
6) 50% DMSO: KCl+Tris-Cl Composition #1 was the ink used for the previous print runs. Since the precipitated salt in composition #1 had been identified as Na citrate the new compositions were modified to circumvent the precipitation of Na citrate salt. The concentration of the Na citrate salt is 10 times lower than the concentration of the NaCl in the SSC based composition. It was hypothesized that the Na+cations from the NaCl could potentiate the precipitation of the citrate by exceeding the solubility product of the citrate in the ink. Hence in composition #2 the NaCl of the SSC based salts was interchanged for the KCl salt to explore the potential for improved solubility. Composition #3 was designed to replace the Na citrate with K citrate to eliminate the presumed common ion effect. Composition #4 was a 2-fold dilution of the 1×SSC based ink. This composition contained half the amount of salt as the other inks. Composition #5 removed the Na citrate completely. Composition #6 was a modification of the KCl+Tris-Cl based ink used by the Institute of Genomic Research (TIGR). The total salt concentration in this ink was higher than that used by TIGR to enable dot detection by the 100% Dot Inspection System.

A 1.5 kB fragment of DNA obtained as a PCR amplified product from pBR plasmid DNA was suspended in the different ink compositions. The same DNA fragment was printed in the different ink compositions and the performance of the ink was evaluated by carrying out hybridizations with 20 picomoles (with respect to the dye) of a 1.5 kB DNA fragment that incorporated the Cy3 fluorophore.

Figure 1A:
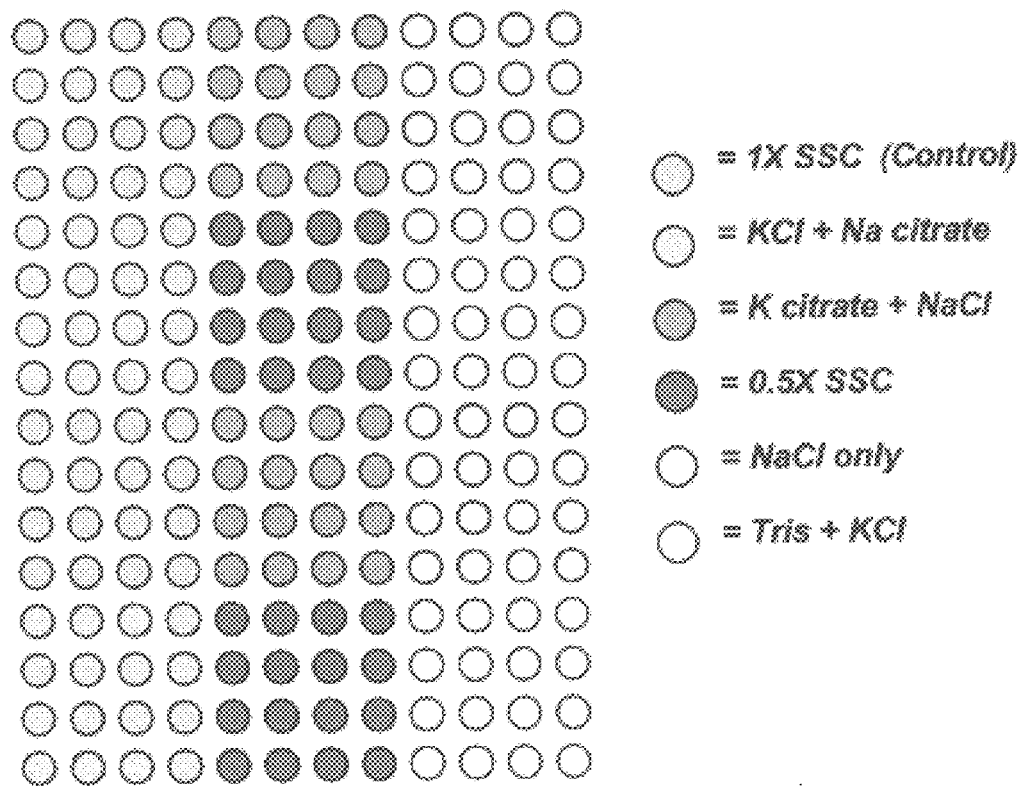
FIG. 1A depicts the grid layout for the DNA printed with six different ink compositions set forth in the Examples.
Figure 1B:
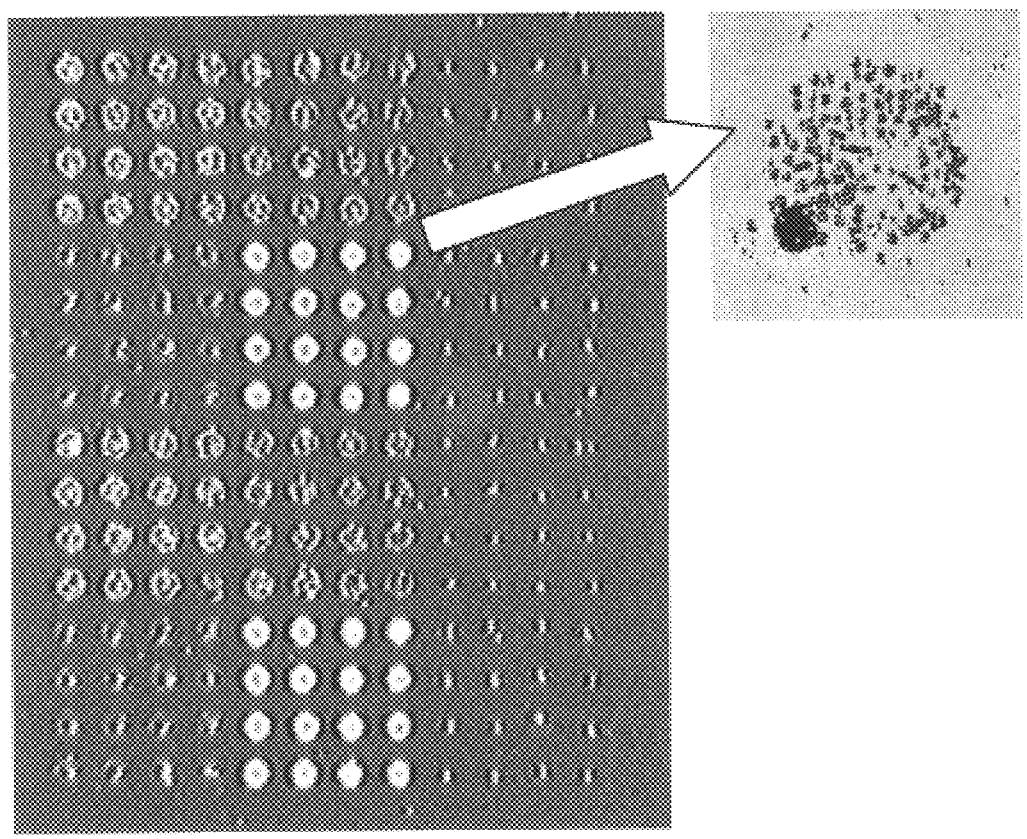
FIG. 1B is an image of the printed dots from the 100% Dot Inspection System. The inset shows a microscopic image of the fine crystalline deposits of the 0.5×SSC salt in the printed dot.

The expected grid layout from the printing experiment is represented in FIG. 1A. The raw image of the printed dots as imaged by the 100% Dot Inspection System is shown in FIG. 1B. The image indicates that the ink containing the lower concentration of SSC (0.5×) provides the best contrast for the optical detection system. The inset in FIG. 1B shows the morphology of the salt deposits obtained with the 0.5×SSC composition. In comparison to the salt deposits in the other inks, the salt crystals in the 0.5× composition are small and appear to enable better diffraction of light. The better contrast obtained with the composition containing the lower amount of salt was unexpected.

Figure 2A:
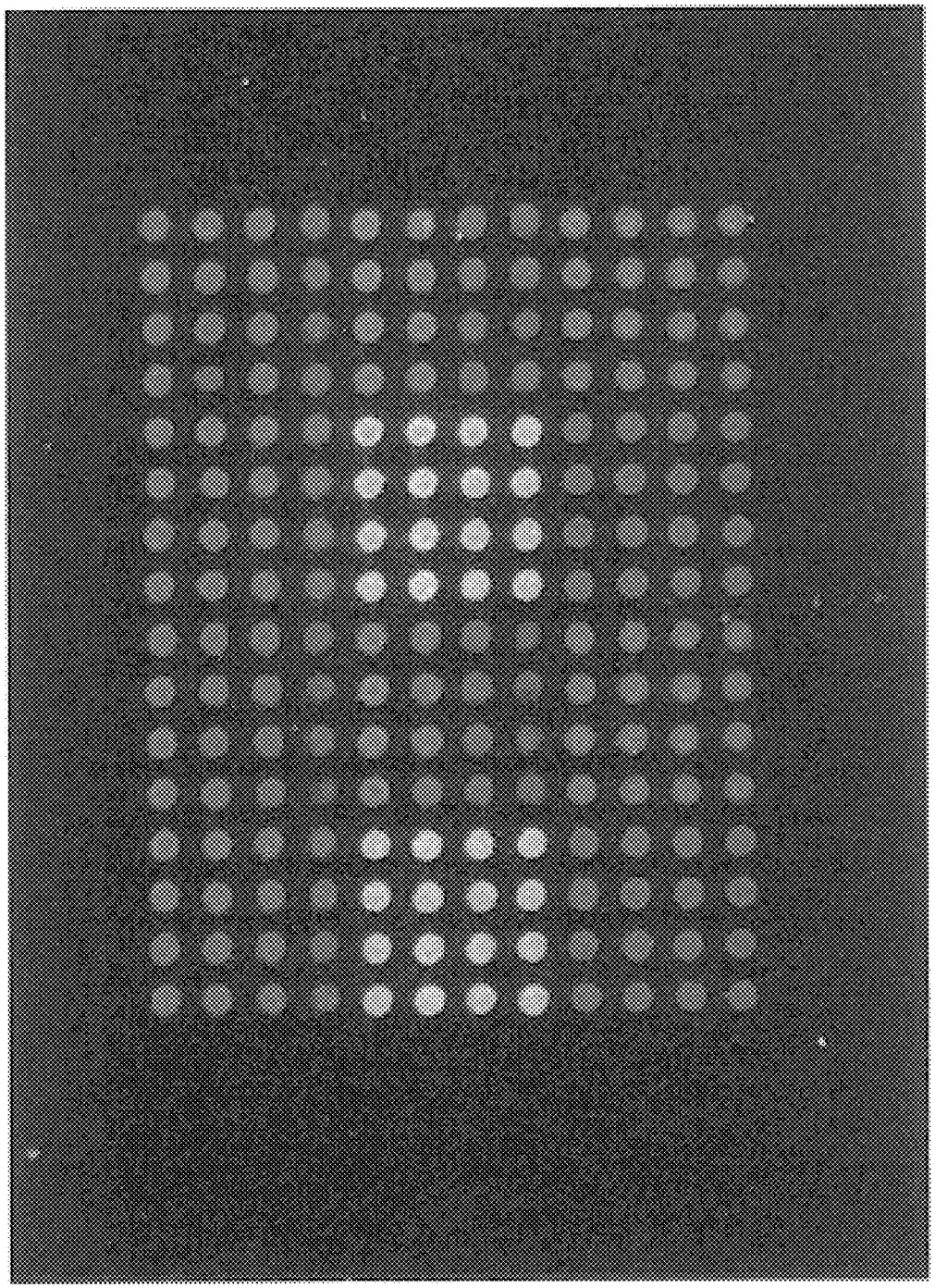
FIG. 2A represents a pseudo-color image of the hybridization signals obtained from hybridization on CMT-GAPS™ slides printed with DNA in the six different inks. The hybridizations were carried out with fluorescently labeled DNA in which the Cy3 label is incorporated into the DNA. The slide was scanned on Scan Array 3000 (General Scanning Inc.) at a laser power setting of 100 and PMT (photomultiplier) setting of 92.
Figure 2B:
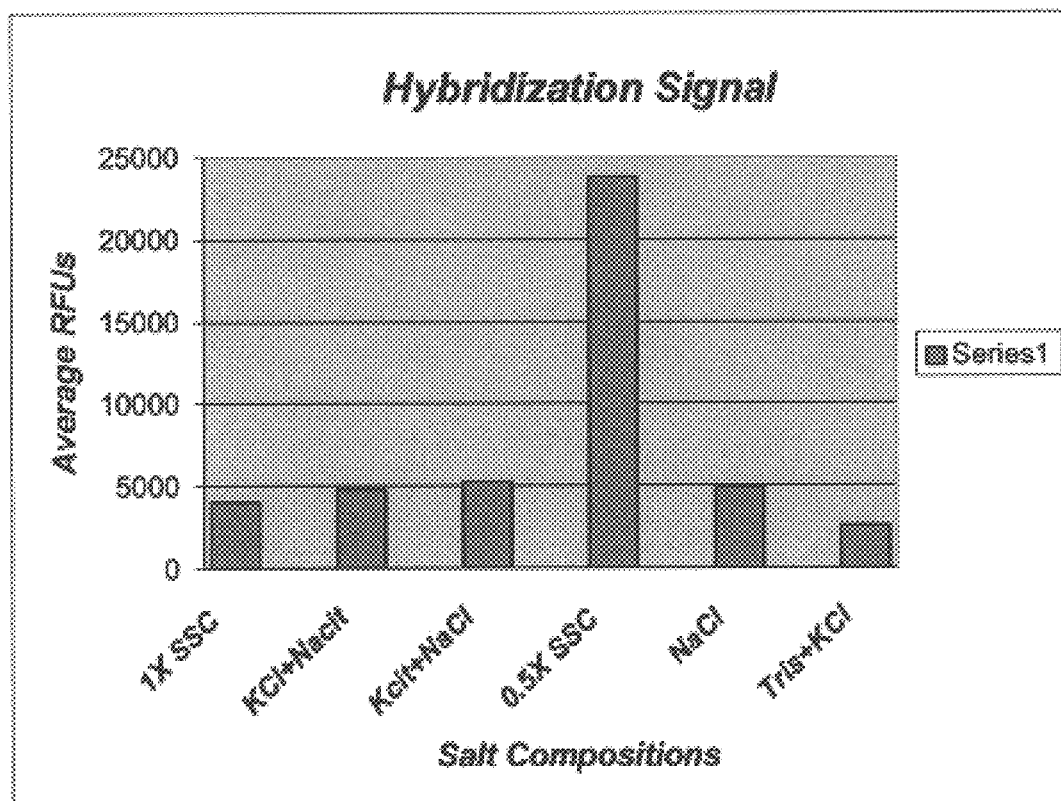
FIG. 2B is a histogram representing the average of the relative fluorescence units (RFUs) obtained from hybridization signals from each of the different inks used for printing. Since the same DNA fragment was printed using the different inks, the differences in signal are due to differences in the wettability and the hybridization efficiency of the printed DNA. The data indicates that the 50% DMSO:SSC (0.5×) ink exhibits a five times greater signal than that obtained with the 50% DMSO:SSC (1×) ink.

The false color image obtained from the hybridization experiments on arrays printed with the above inks is shown in FIG. 2A. Quantification of the data (FIG. 2B) indicated that the hybridization response from all inks except the ink containing the lower concentration of SSC (0.5×) were comparable to the 1×SSC composition that was used as a control. The signal from the 0.5×SSC ink was approximately five times greater than that obtained with the 1× ink. While not wishing to be bound by theory, the enhancement in signal could be due to better wettability of the pins and the slides by the 0.5×SSC based ink. It could also be due to the enhanced retention of the DNA on the positively charged GAPS surface. It is conceivable that a higher salt concentration shields the electrostatic interaction that enables the adhesion of the negatively charged DNA molecules to the positively charged surface. The lower concentration of salts in the 0.5×SSC ink could thereby facilitate better adhesion of the DNA to the substrate.

Figure 3:
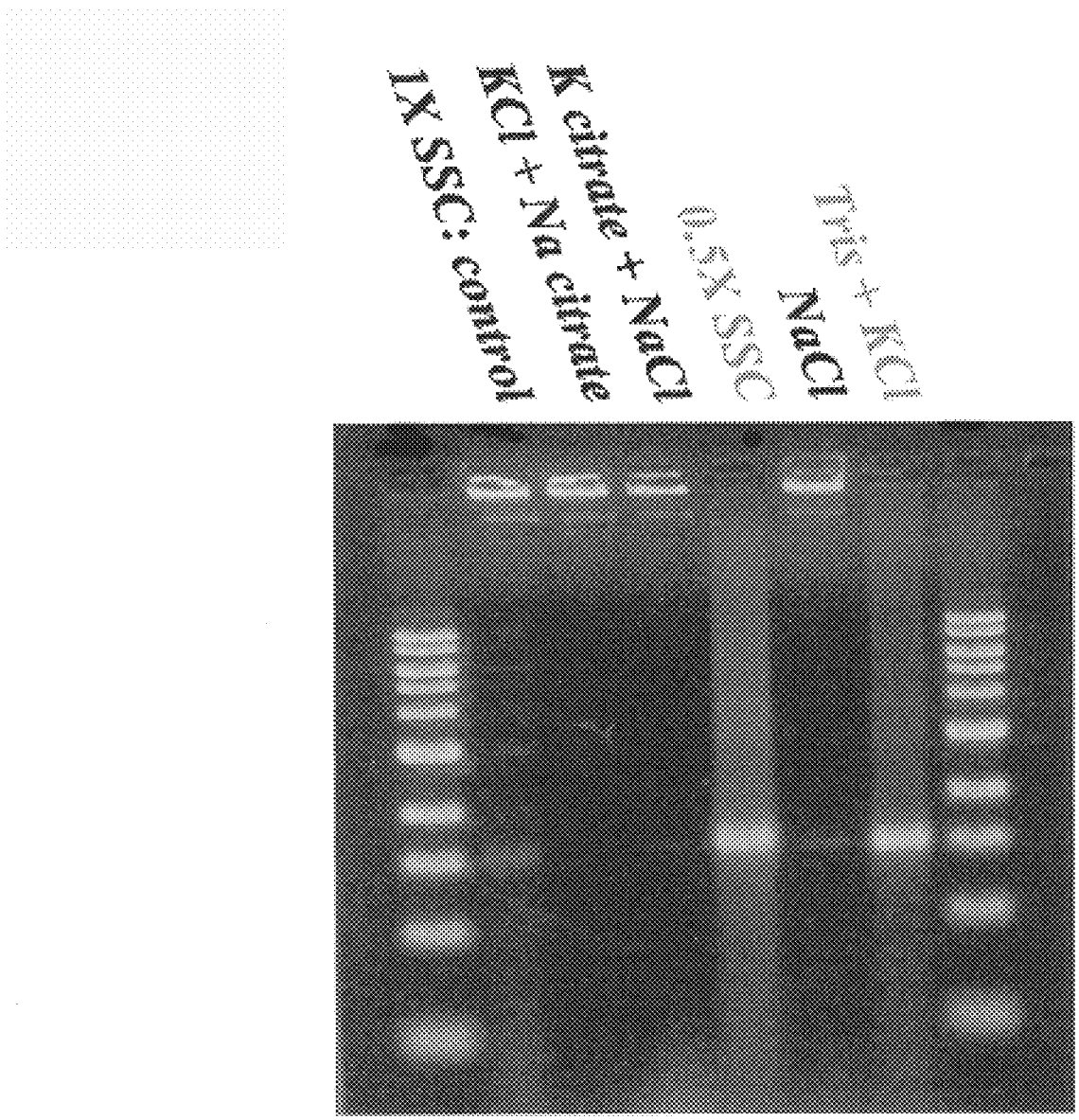
FIG. 3 is an image of an agarose gel depicting the relative electrophoretic mobility of the DNA samples in the different inks 7 days after printing. The DNA in the 0.5×SSC and Tris-Cl+KCl based DMSO inks exhibit the normal mobility expected for a 1.5 KB DNA fragment. The DNA suspended in all other inks is retained in the wells of the gel. This anomalous mobility is generally attributed to large aggregates of DNA that are presumably formed over time due to an unstable ink medium.

To test the stability of the various inks, the DNA samples in the six different inks and a DNA ladder (marker) were run on a 1% agarose gel seven days after the printing experiment. FIG. 3 shows an image of the gel. The gel clearly indicates that all inks except the inks containing 0.5×SSC and Tris-Cl+KCl salts exhibited an anomalous pattern that was indicative of DNA aggregation. The DNA suspended in the 0.5×SSC ink exhibited the expected mobility for a 1.5 kB fragment as based on comparisons with the DNA marker that was loaded alongside.

The data gathered on the dot detection, hybridization performance, and DNA stability of the various inks indicated that the 50% DMSO:SSC (0.5×) composition containing a final concentration of 75 mM NaCl and 7.5 mM sodium citrate was a significant improvement over the typical inks used for HDA applications.

Sample Preparation

This section describes the preparation of the compositions and the bio-formatting of DNA solutions. All inks had the following features in common 1) All inks contained 50% DMSO v/v.
2) All inks contained EDTA (ethylene diamine tetraacetic acid) in a final concentration of 0.5 mM.
3) All inks except composition #4 contained a net salt concentration of 13.178 g/l. Composition #4 contained a salt concentration of 6.589 g/l.

The aqueous component of the inks were prepared as follows

Composition 1: Control 5.0 ml of 20.0×SSC stock solution (Gibco BRL, catalog # 15557-044)

100 Tl of 0.5 M di sodium EDTA stock solution (Gibco BRL, catalog # 15575-038)

All were added to a 50 Ml Corning polypropylene tube and fresh 18 mOhm water was added up to a volume of 50 ml.

Composition 2

0.8766 g of KCl (Sigma, catalog #P-9541)

0.4412 g of sodium citrate (Sigma, catalog 3674)

100 Tl of 0.5M di sodium EDTA stock solution (Gibco BRL, catalog # 15575-038)

All were added to a 50 ml Corning polypropylene tube and fresh 18 mOhm was added up to a volume of 50 ml.

Composition 3

0.4412 g of K citrate (Sigma, catalog # C-3029)

3 ml of 5M NaCl stock solution (Sigma, catalog # S 5150)

100 Tl of 0.5 M di sodium EDTA stock solution (Gibco BRL, catalog # 15575-038)

All were added to a 50 ml Corning polypropylene tube and fresh 18 mOhm water was added to a volume of 50 ml.

Composition 4

2.5 ml of 20.0×SSC stock solution (Gibco BRL, catalog # 15557-044)

100 Tl of 0.5 M di sodium EDTA stock solution (Gibco BRL, catalog # 15575-038)

All were added to a 50 ml Corning polypropylene tube and fresh 18 mOhm water was added up to a volume of 50 ml.

Composition 5

4.5 ml of 5 M NaCl stock solution (Sigma, catalog # S-5150)

100 Tl of 0.5 M di sodium EDTA stock solution (Gibco BRL, catalog # 15575-038)

All were added to a 50 ml Corning polypropylene tube and fresh 18 mOhm water was added up to a volume of 50 ml.

Composition 6

0.8766 g of KCl (Sigma, catalog #P-9541)

2.8 ml of a 1M stock solution of Tris-Cl (Sigma, catalog # T-3038)

100 Tl of 0.5 M di sodium EDTA stock solution (Gibco BRL, catalog # 15575-038)

All were added to a 50 ml Corning polypropylene tube and fresh 18 mOhm water was added up to a volume of 50 ml.

The final ink compositions were prepared by adding 25 ml DMSO (Sigma, catalog # D-8418) to 25 ml of the aqueous stocks (prepared as described above) in a 50 ml Corning polypropylene tube. The solutions were mixed by inverting the tubes 10 times. These ink compositions were stored at 4C for 36 hours and were subsequently used for bioformatting the DNA. 500 Tl of ink was added to a microfuge tube containing 125 Tg (in dried form) of the DNA and used to resuspend the DNA. 10 Tl of the DNA solution (final DNA concentration=0.25 Tg/Tl) was transferred to the wells in the appropriate plates. All six compositions were printed on CMT-GAPS™ slides (Corning Inc.) using a solid pin printer from Intelligent Automation Systems (IAS), Cambridge, Mass. The final concentrations of the ink compositions are tabulated below:

| Composition # Plate # | Aqueous Components | Final molar concentration in 50% DMSO: Aqueous ink | Final molal concentration of salt in 50% DMSO: Aqueous ink | Molecular weight of aqueous components |
|---|---|---|---|---|
| Composition #1 (Control) Plate #1 | NaCl Na citrate.2H$_2$O EDTA.2Na | 150.0 mM 15.0 mM 0.5 mM | 8.766 g/l 4.412 g/l | 58.44 g 294.1 g 372.2 g |
| Composition #2 Plate #1 | KCl Na citrate.2H$_2$O EDTA.2Na | 117.6 mM 15.0 mM 0.5 mM | 8.766 g/l 4.412 g/l | 74.55 g 294.1 g 372.2 g |
| Composition #3 Plate #2 | NaCl K citrate.2H$_2$O EDTA.2Na | 150.0 mM 13.6 mM 0.5 mM | 8.766 g/l 4.412 g/l | 58.44 g 324.4 g 372.2 g |
| Composition #4 Plate #2 | NaCl Na citrate.2H$_2$O EDTA.2Na | 75.0 mM 7.5 mM 0.5 mM | 8.766 g/l 4.412 g/l | 58.44 g 294.1 g 372.2 g |
| Composition #5 Plate #3 | NaCl EDTA.2Na | 450 mM 0.5 mM | 13.178 g/l | 58.44 g 372.2 g |
| Composition #6 Plate #3 | KCl Tris-Cl EDTA.2Na | 117.6 mM 28.0 mM 0.5 mM | 8.766 g/l 4.412 g/l | 74.55 g 157.6 g 372.2 g |

Example 2

50% DMSO:SSC based inks with varying concentrations of the SSC were used to bio-format a 1.5 kb fragment of DNA. These DNA inks were printed on the CMT-GAPS (TM) slides with a robotic printer using stainless steel pins. The grid layout for the different inks is described in the Description of the Drawings.

A portion of the grid on the printed slide was stained with sybr gold dye. Sybr gold is a fluorescent dye and is used as a qualitative indicator of the presence of DNA. The image (FIG. 4B) indicates that significant amounts of DNA is deposited and retained with 50% DMSO based inks with SSC concentrations of less than 0.5× compared to inks containing no salt. The dotted circles on the grid indicates the set of printed DNA with 50%DMSO:SSC at 1×SSC concentration that did not stain significantly with sybr gold. The morphology of spots with no SSC in the ink is different from those containing SSC.

The printed slides were hybridized with a Cy3 labeled 1.5 kB DNA. The slide was scanned on Scan Array 3000 (General Scanning Inc.). The data from the image indicates that comparable hybridization signal is obtained with 50% DMSO:SSC inks containing SSC at concentrations between 0.5× and 0.1×SSC. DMSO:SSC compositions containing salt concentrations that is in between 1× and 0.5× have hybridization signals that is lower than that obtained with 0.5× and higher than that obtained with 1.0×. Ink compositions having no salt have poor dot morphology.

Example 3

A series of DMSO and SSC containing inks were prepared in which the DMSO content varied from 10% to 80%. The salt concentration in these inks was kept constant at 0.25× to establish the range of acceptable DMSO content. A 1.5 kB fragment of DNA (derived from the pBR plasmid) was bio-formatted in these inks at a final concentration of 0.25 mg/ml and printed on CMT-GAPS (TM) slides using stainless steel solid pin flexys printer (from Genomics Solution Inc.). The printed slides were hybridized with a PCR probe made by incorporating Cy3-dCTP into the 1.5 kB fragment. 20 picomoles of the Cy3 labeled probe was suspended in 25 Tl hybridization buffer ( 3×SSC, 25% formamide, 0.1% SDS). The hybridization was carried out in a sealed hybridization chamber (Corning Inc.) in a water bath at 42° C. for ~14 hours. The hybridized slides were washed with 2 consecutive washing steps to remove excess probe on the slide and eliminate non-specific binding of the probe to the target printed DNA. The first wash solution contained 1×SSC, 0.1%SDS and the hybridized slides were washed for 10 minutes at 42° C. The second wash solution contained 0.1×SSC and the washing was carried out at room temperature for 10 minutes. The slides were dried with nitrogen subsequently scanned on the Scan Array 3000 (General Scanning Inc.). The results are set forth in FIG. 5.

It will be apparent to one skilled in the art that the manner of making and using the claimed invention has been adequately disclosed in the above-written description of the preferred embodiment(s) taken together with the drawings; and that the above described preferred embodiment(s) of the present invention are susceptible to various modifications, changes, and adaptations, and the same are intended to be comprehended within the meaning and range of equivalents of the appended claims.

Further, although a number of equivalent components may have been mentioned herein which could be used in place of the components illustrated and described with reference to the preferred embodiment(s), this is not meant to be an exhaustive treatment of all the possible equivalents, nor to limit the invention defined by the claims to any particular equivalent or combination thereof. A person skilled in the art would realize that there may be other equivalent components presently known, or to be developed, which could be used within the spirit and scope of the invention defined by the claims.

What is claimed is:

1. A medium for suspending a solution of nucleic acid, the medium having a composition comprising: dimethylsulfoxide (DMSO) in a range from about 30% to about 80% by volume, sodium chloride/sodium citrate salt containing buffer (SSC) at a final concentration of from about 0.1× (15 mM sodium chloride+1.5 mM sodium citrate) to about 0.8× in salts (120 mM sodium chloride+12 mM sodium citrate), water, and nucleic acid, wherein said nucleic acid denatures to provide for more favorable hybridization.

2. The medium according to claim 1, wherein said solution induces said nucleic acid to show increased fluorescent signal when hybridized.

3. The medium according to claim 1, wherein said medium comprises about 40% to about 80% DMSO by volume and SSC at a final concentration from about 0.1× to about 0.5×.

4. The medium according to claim 1, wherein said medium comprises about 40% to about 60% DMSO by volume and SSC at a final concentration from about 0.25× to about 0.5×.

5. The medium according to claim 1, wherein said medium comprises about 50% DMSO by volume and SSC at a final concentration from about 0.1× to about 0.5×.

6. The medium according to claim 1, wherein said composition may also include EDTA in a final concentration between 0 and 4 mM.

7. The medium according to claim 1, wherein said nucleic acid is at a concentration ranging from about 0.01 mg/ml to about 0.5 mg/ml.

8. The medium according to claim 1, wherein the nucleic acid is a double stranded DNA, RNA, or an oligonucleotide.

9. The medium according to claim 1, wherein said composition enables long-term storage and preserves integrity of nucleic acid without instability by precipitation or aggregation of said nucleic acid.

10. The medium according to claim 9, wherein said composition enables long term storage of over 1 month.

11. The medium according to claim 1, wherein said medium absorbs moisture from air to overcome a net loss of solvent due to evaporation of said water component.

12. The medium according to claim 1, wherein said nucleic acid may be suspended in said medium for at least 5 days prior to depositing on a solid support.

13. A method for depositing nucleic acid on a solid support, said method comprising:
    providing a medium according to that of claim 1, wherein said nucleic acid shows increased fluorescent signal when hybridized; and
    contacting said medium to said solid support.

14. The method according to claim 13, wherein the contacting step further comprises immersing a tip of a pin into said medium; removing said tip from said medium with said medium adhered to said tip; and transferring said solution to said solid support.

15. The method according to claim 13, wherein said contacting step is repeated a plurality of times to provide an array of nucleic acid.

16. The method according to claim 13, wherein said nucleic acid is suspended in said medium for at least 5 days prior to contacting with said solid support.

17. The method according to claim 13, wherein said medium comprises about 40% to about 80% DMSO by volume and SSC at a final concentration from about 0.1× to about 0.5×.

18. The method according to claim 13, wherein said medium comprises about 40% to about 60% DMSO by volume and SSC at a final concentration from about 0.25' to about 0.5×.

19. The method according to claim 13, wherein said medium comprises about 50% DMSO by volume and SSC at a final concentration from about 0.1× to about 0.5×.

20. The method according to claim 13, wherein said nucleic acid is at a concentration ranging from about 0.01 mg/ml to about 0.5 mg/ml.

21. The method according to claim 13, wherein the nucleic acid is a double stranded DNA, RNA, or an oligonucleotide.

22. The method according to claim 13, wherein said solid support is a membrane or glass substrate.

23. The method according to claim 22, wherein said glass substrate is a planar solid glass surface or three-dimensional porous glass surface.

24. The method according to claim 23, wherein said glass substrate comprises an aminated surface.

25. The method according to claim 24, wherein said aminated surface is coated with an aminating agent comprising either gama-aminopropyl-silane or polylysine.

* * * * *

UNITED STATES PATENT AND TRADEMARK OFFICE
CERTIFICATE OF CORRECTION

PATENT NO. : 6,558,907 B2
DATED : May 6, 2003
INVENTOR(S) : Melanie C. Caracci et al.

It is certified that error appears in the above-identified patent and that said Letters Patent is hereby corrected as shown below:

<u>Column 14,</u>
Line 16, please delete "0.25'" and add -- 0.25X --

Signed and Sealed this

Second Day of March, 2004

JON W. DUDAS
*Acting Director of the United States Patent and Trademark Office*